United States Patent [19]
Kaplan et al.

[11] 3,993,995
[45] Nov. 23, 1976

[54] RESPIRATION MONITOR

[75] Inventors: Gerald Stanley Kaplan, Lawrenceville, N.J.; Alvin Seymour Clorfeine, Adelphi, Md.

[73] Assignee: RCA Corporation, New York, N.Y.

[22] Filed: Dec. 8, 1975

[21] Appl. No.: 638,847

[52] U.S. Cl. .............................. 343/7 ED; 128/2 R
[51] Int. Cl.² ........................ A61B 5/08; G01S 9/04
[58] Field of Search .................... 128/2 R, 2 C, 2 V; 343/7 ED

[56] References Cited
UNITED STATES PATENTS

| | | | |
|---|---|---|---|
| 3,524,058 | 8/1970 | Robertson et al. | 128/2 R X |
| 3,796,989 | 3/1974 | Ravas et al. | 343/7.7 X |
| 3,802,253 | 4/1974 | Lee | 128/2 V X |
| 3,856,985 | 12/1974 | Yokoi et al. | 128/2 V X |
| 3,864,660 | 2/1975 | Ranalli et al. | 128/2 V X |

FOREIGN PATENTS OR APPLICATIONS 1,080,982   8/1967   United Kingdom ................ 128/2 R

OTHER PUBLICATIONS

"Ultrasonic Recording of Fetal Breathing" by H. B. Meire et al., British Journal of Radiology, vol. 48, No. 570, pp. 477–480, Jan. 1975, Patent Associated Literature B010-7506-B.

*Primary Examiner*—Malcolm F. Hubler
*Attorney, Agent, or Firm*—Edward J. Norton; Joseph D. Lazar; Michael A. Lechter

[57] ABSTRACT

An apparatus for automatically monitoring the respiration of a subject requiring no physical connection to the subject. The use of such apparatus for automatically triggering an x-ray machine at instants of respiration extrema is also disclosed.

5 Claims, 3 Drawing Figures

RESPIRATION MONITOR

BACKGROUND OF THE INVENTION

1. Field of the Invention

The present invention is directed to respiration monitors and, in particular, to automatic x-ray machine triggering systems for use on uncooperative subjects.

2. Description of the Prior Art

In the medical field, it is frequently desirable to monitor a given subject's respiration. For example, x-ray pictures for study of the lungs should be taken at points of maximum inhalation when the lungs are fully inflated. Similarly, x-ray pictures for examination of the area surrounding the lungs should be taken at points of maximum exhalation, when the lungs are fully deflated. Such instants of maximum inhalation or exhalation shall hereinafter be collectively termed "instants of respiration extrema." In practice, the x-ray machine operator instructs the subject to inhale or exhale and maintain that condition while the x-ray picture is taken. A problem, however, rises when a chest x-ray is taken of an uncooperative subject, such as an unconscious adult, an infant or an animal. U.S. Pat. No. 3,524,058 issued Aug. 11, 1970 to Robertson et al. is directed to a respiration monitor for use in an x-ray triggering system whereby instants of maximum inhalation and exhalation are detected to automatically trigger the x-ray machine. Such respiration monitor, however, requires a physical connection to the subject's body. Specifically, electrodes are connected to the subject to direct an electric current through a particular portion of the subject's body, and the modulation of the current by the subject's body is monitored to detect points of maximum inhalation or exhalation. Other respiration monitors utilize masks and nasal insertions. Such prior art systems, in requiring such physical connections to the subject, have disadvantages that render the use of such systems undesirable.

SUMMARY OF THE INVENTION

The present invention is directed to a respiration monitor requiring no physical connection to the subject. A probe signal is transmitted to illuminate a body portion of the subject and reflections therefrom are received by the monitor. Signals respectively indicative of the cosine and sine of the phase difference between the probe signal and reflected signal are generated, and an output signal, for example, for triggering an x-ray unit, is generated only when the time derivative of both the sine and cosine signals are concurrently substantially zero, indicating an instant of respiration extrema.

DETAILED DESCRIPTION OF PREFERRED EMBODIMENTS

Figure 1:
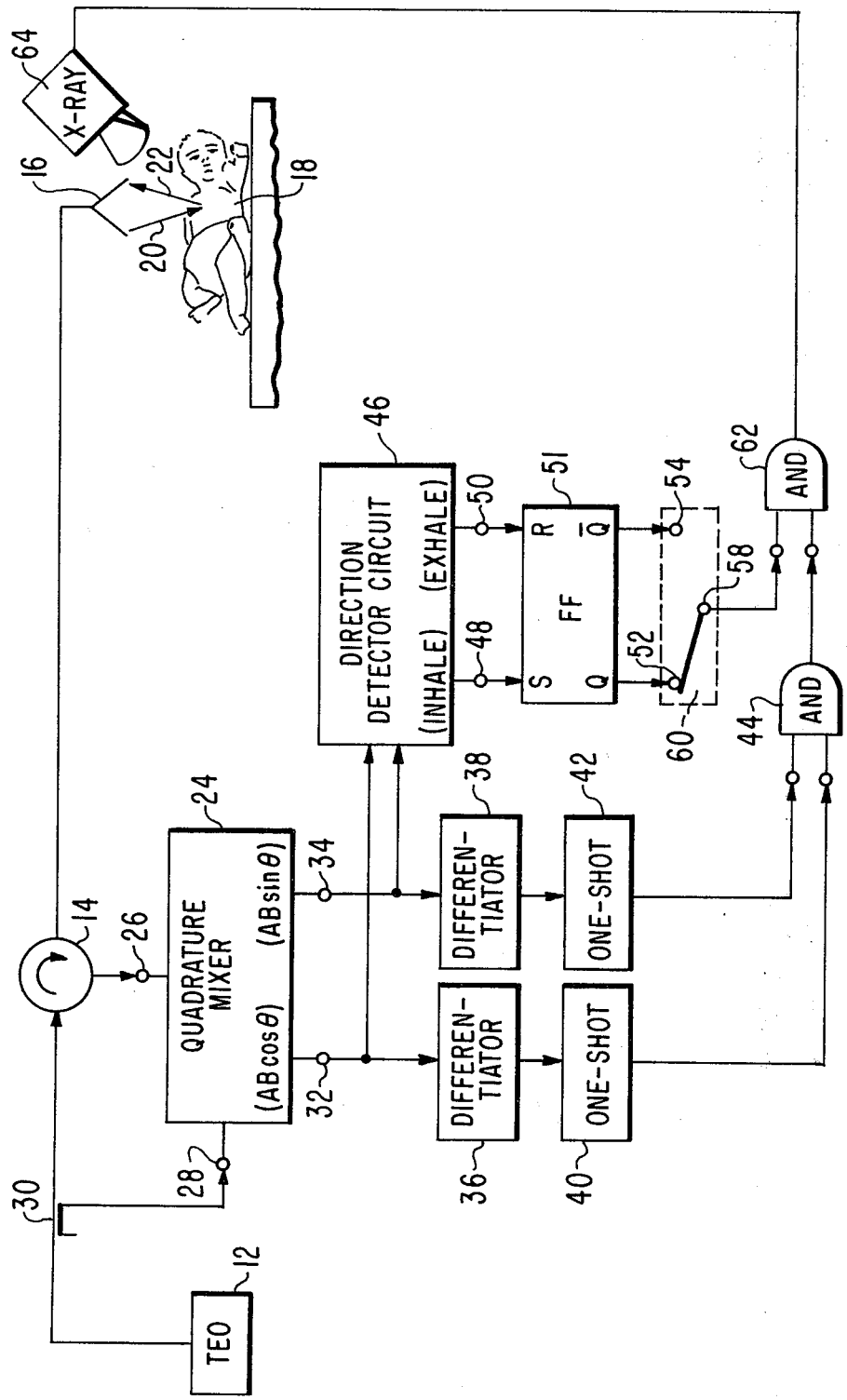
FIG. 1 is a block diagram of a respiration monitor in accordance with the present invention.

Referring to FIG. 1, a transferred electron oscillator (TEO) 12 is coupled through a circulator 14 to an antenna 16. Antenna 16 is preferably a printed circuit corporate feed antenna such as described in U.S. Pat. No. 3,587,110 issued June 22, 1971 to O. M. Woodward. Antenna 16 is disposed to illuminate a predetermined body portion, typically the chest or abdomen, of a subject 18 with a radiated probe signal 20. Signals 22 reflected from subject 18 in response to probe signal 20 are received by antenna 16 and routed via circulator 14 to a first input terminal 26 of a quadrature mixer 24. It should be appreciated that separate transmit and receive antennas may be employed, if desired, with the transmit antenna directly coupled to TEO 12 and the receive antenna coupled directly to input terminal 26 of quadrature mixer 24.

Quadrature mixer 24 has, in addition to input terminal 26, second input terminal 28 and first and second output terminals 32 and 34. Embodiments of quadrature mixer 24 will be described below in conjunction with FIGS. 2 and 3. Applied to second input terminal 28 is a sample of the TEO output signal derived from the TEO output signal by a directional coupler 30. The sampled TEO signal shall hereinafter be designated the "probe sample." First and second output terminals 32 and 34 are respectively coupled to differentiators 36 and 38. Differentiators 36 and 38 are suitably high pass filters and are respectively coupled, in turn, to conventional one shots 40 and 42. One shots 40 and 42 are coupled to the respective input terminals of a two input AND gate 44. Quadrature mixer output terminals 32 and 34 are also respectively coupled to a suitable direction of motion detector circuit 46 to indicate inhalation (ascent) and exhalation (descent) of the patient. A detector to perform such functions is described in Skolnik, "Introduction to Radar Systems" McGraw-Hill, 1962, pp. 83 and 84, in conjunction with FIG. 3.9 of that reference. Direction detector 46 has two output terminals 48 and 50 which are respectively connected to the set (s) and reset (r) terminals of an RS flip-flop (FF) 51. The Q and $\overline{Q}$ output terminals of FF 51 are coupled to the respective throw terminals 52 and 54 of a single-pole, double-throw switch 60. The pole terminal 58 of switch 60 is coupled to one input terminal of a two input AND gate 62, the other input of which is coupled to the output terminal of AND gate 44. The output terminal of AND gate 62 is coupled to suitable utilization means, such as the activator of an x-ray unit 64.

Figure 2:
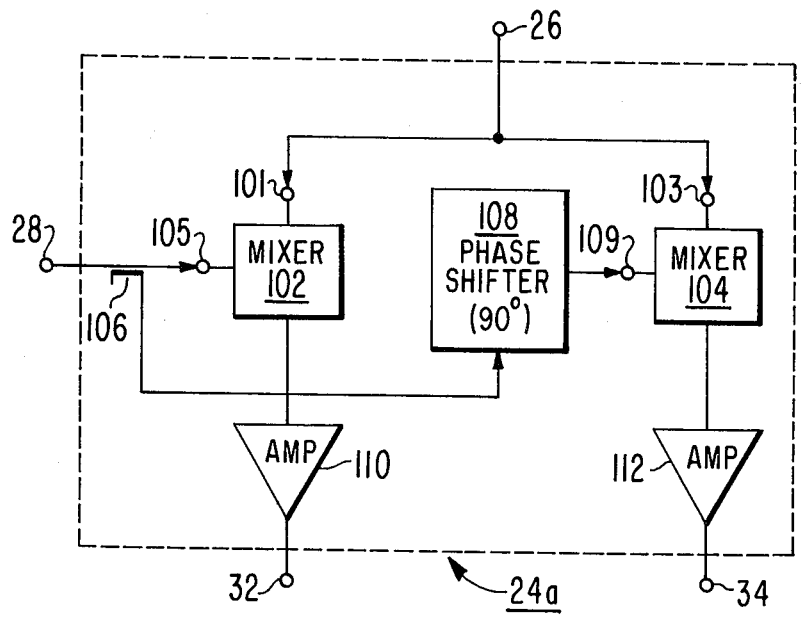
FIGS. 2 and 3 are block diagrams of alternative embodiments of quadrature mixers for use in the respiration monitor of FIG. 1.
Figure 3:
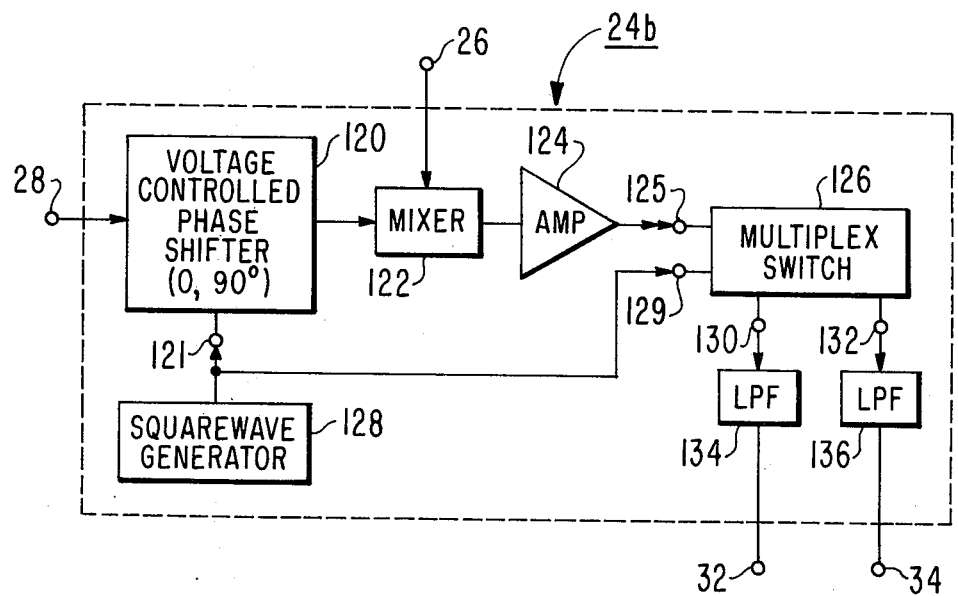

FIGS. 2 and 3 depict alternative embodiments 24a and 24b of quadrature mixer 24. Referring to FIG. 2, reflected signals 22, as applied to input terminal 26 of quadrature mixer 24 are applied to terminals 101 and 103 of first and second conventional mixers 102 and 104. The probe sample is applied to a second input terminal 105 of mixer 102 via terminal 28 and, by means of a directional coupler 106, through a conventional phase shifter 108 to a second input terminal 109 of mixer 104. Output signals of mixers 102 and 104 are suitably amplified by a pair of balanced and matched amplifiers 110 and 112. Amplifiers 110 and 112 must be balanced and matched lest erroneous phase differences be introduced between the first and second output signals. The output terminals of amplifier 110 and 112 are respectively utilized as output terminals 32 and 34 of quadrature mixer 24.

Referring to FIG. 3 an embodiment 24b of quadrature mixer 24, not requiring a pair of balanced amplifiers is described. The probe sample, as applied to input terminal 28, is passed through a voltage-controlled phase shifter 120 to a conventional mixer 122, the other input signal to mixer 122 being received via input terminal 26 of quadrature mixer 24. The output signal of mixer 122, suitably amplified by amplifier 124, is applied to the input terminal 125 of a suitable voltage-controlled multiplex switch 126. Multiplex switch 126 also has a switching control terminal 129 and first and second output terminals 130 and 132. A common control signal, typically a square wave generated by square wave generator 128, is applied to voltage-controlled phase shifter 120, at a control terminal 121, and multiplex switch 126, at its control terminal 129. Such square wave typically maintains a 50 percent duty cycle and amplitudes such that a 90° differential phase shift is effected by phase shifter 120. Multiplex switch output terminals 130 and 132 are respectively connected to low pass filters 134 and 136. The outputs of low pass filters 134 and 136 are provided at the output terminals 32 and 34 of quadrature mixer 24.

Referring again to FIG. 1, the operation of the respiration monitor will now be described. TEO 12 generates a signal, typically radio frequency, which is routed through circulator 14 to antenna 16. Antenna 16 transmits the TEO output signal as probe signal 20 to illuminate, for example, the chest or abdoman of subject 18. Reflected signals 22 from subject 18 are received by antenna 16 and routed by circulator 14 to quadrature mixer 24. The round trip transmit time between antenna 16 and subject 18 produces a phase difference $\theta$ between probe signal 20 and reflected signal 22. Such phase difference $\theta$ is a function of the distance, ($d$), between antenna 16 and the illuminated body portion of subject 18, as expressed by the following equation:

$$\theta = \frac{4\pi d}{\lambda} \qquad (1)$$

where $\lambda$ is the wavelength of probe signal 20. The distance $d$, and hence the phase $\theta$, changes in accordance with physical movement of the subject 18. Assuming no other physical movement of the subject is occurring, the distance $d$ will vary as a function of respiration. Respiration extrema define thus distance ($d$) extrema and phase ($\theta$) extrema. Accordingly, instants of respiration extrema are indicated when the time derivative of the distance, and hence the time derivative of $\theta$, viz., $d\theta/dt$, are equal to zero.

A conventional mixer, such as mixers of the type used in homodyne ranging systems, generates an output voltage equal to the product of the amplitude of the respective signals applied thereto times the cosine of the phase angle between such input signals. When such an output voltage is the sole measure of $\theta$ in a respiration monitor an ambiguity with respect to instants of respiration extrema occurs; the time derivative of such an output voltage is not only a function of $d\theta/dt$ but also a function of sin $\theta$ and, accordingly, assumes a zero value when either sin $\theta$ or $d\theta/dt$ goes to zero.

In accordance with the present invention, to eliminate such ambiguity, quadrature mixer 24 generates, at output terminals 32 and 34, first and second output signals, the first signal being indicative of the cos $\theta$ (similar to the output signal of a conventional mixer noted above), and the second output signal being phase shifted with respect to the first, preferably substantially in quadrature, such that the second output signal is indicative of the sin $\theta$. The first and second output signals are hereinafter respectively referred to as the "in-phase" and "quadrature" output signals. Specifically, the respective voltages $V_1$ and $V_2$ of such in-phase and quadrature output signals may be expressed as:

$$V_1 = AB \cos \theta \qquad (2)$$

$$V_2 = AB \sin \theta \qquad (3)$$

where A and B are respectively the amplitudes of the probe sample as derived by directional coupler 30 and reflected signals 22.

Referring again to FIG. 2, quadrature mixer embodiment 24b effects the generation of such in-phase and quadrature signals as follows. As noted above, the output signal of a conventional mixer such as mixer 102 is indicative of cos $\theta$, and maintains a voltage ($V_1$) in accordance with equation (2) above. Phase shifter 108 effects a 90° phase shift between the output signals of mixers 102 and 104. The output voltage $V_2$ of mixer 104 is thus expressed mathematically as:

$$V_2 = AB \cos (\theta - 90°) = AB \sin \theta \qquad (4)$$

Thus, embodiment 24a generates in-phase and quadrature output signals at output terminals 32 and 34.

Now with reference to FIG. 3, the generation of such first and quadrature signals by embodiment 24b of quadrature mixer 24 is described. Phase shifter 120 operates to shift alternately the phase of the probe sample by a first and second predetermined phase, the differential phase between such first and second phase being substantially 90°, in accordance with the control signals from square wave generator 128. Accordingly, the output signal of conventional mixer 122 is alternately indicative of cos $\theta$ and cos ($\theta - 90°$) switching therebetween in accordance with the frequency of the control signal generated by square wave generator 128. As noted in equation 4, cos ($\theta - 90°$) is equal to sin $\theta$. Multiplex switch 126 operates to apply alternately the mixer output signal, as amplified by amplifier 124, to the respective multiplex switch output terminals 130 and 132, in accordance with the frequency of the control signal from square wave generator 128. Thus, the signals at terminals 130 and 132 are, in effect, a square wave carrier having the frequency and duty cycle of the control signal generated by square wave generator 128, amplitude modulated by respective signals indicative of cos $\theta$ and sin $\theta$. Low pass filters 134 and 136 operate, in effect, as envelope detectors to remove such square wave carriers and generate the respective output signals indicative of cos $\theta$ and sin $\theta$ at output terminals 32 and 34.

Referring once more to FIG. 1, the mixer 24 in-phase output signal is differentiated by differentiator 36, which triggers one shot 40 when such derivative is substantially equal to zero. As noted above, the derivative $dV_1/dt$ of mixer 24 in-phase output signal is a function of $d\theta/dt$ and sin $\theta$ as expressed in the following equation:

$$\frac{dV_1}{dt} = -AB \frac{d\theta}{dt} \sin \theta \qquad (5)$$

Accordingly, one shot 40 is fired not only when $d\theta/dt$ is equal to zero but also when sin $\theta$ is equal to zero. However, in accordance with the present invention, mixer 24 also generates the quadrature output signal.

Differentiator 38 differentiates such quadrature signal and triggers one shot 42 when the derivative d $V_2$/dt is equal to zero. The derivative of the quadrature output signal is a function of d$\theta$/dt and cos $\theta$ and may be expressed as in the following equation (6):

$$\frac{dV_2}{dt} = AB \frac{d\theta}{dt} \cos \theta \qquad (6)$$

Accordingly, the derivative d $V_2$/dt assumes a zero value, and one shot 42 is fired, when either d$\theta$/dt or cos $\theta$ goes to zero. However, instants when sin $\theta$ and cos $\theta$ assume zero values are mutually exclusive. Hence, the derivatives of the first output signal and the quadrature output signal are concurrently zero only when d$\theta$/dt is equal to zero. Accordingly, one shots 40 and 42 are coupled to AND gate 44, which produces an output signal only when both one shots 40 and 42 are concurrently fired. Thus, the output signal of AND gate 44 is indicative of instants of respiration extrema of subject 18.

The use of quadrature mixer 24 is advantageous in that it facilitates the use of a conventional direction of motion detector (46) such as used in aircraft rate of climb meters. Direction detector 46 generates two output signals. The first output signal assumes a high level value during periods wherein the distance between antenna 16 and the body portion of subject 18 is decreasing, indicating inhalation; the second assumes a high level during periods wherein such distance is increasing, indicating exhalation. FF 51 serves as a latch. Accordingly, the Q and $\overline{Q}$ outputs of FF 51 are respectively indicative of inhalation and exhalation. The desired specie of respiration extrema, as chosen between instants of maximum inhalation and maximum exhalation, is chosen by means of switch 60, whereby the signal indicative of inhalation or exhalation is applied to AND gate 62, which generates an output signal only when d$\theta$/dt assumes a zero value during the chosen phase of respiration. The output signal of AND gate 62 is utilized, for example, to trigger x-ray unit 64.

It should be appreciated that respiration monitor 10 can also be utilized to sound an alarm in the event a subject ceases respiration. In such case the output signals of AND gate 44 are utilized to toggle a flip-flop (not shown), the Q and $\overline{Q}$ output signals of which flip-flop are respectively utilized to start and reset a clocked counter (not shown). If the contents of the counter exceed a predetermined maximum, an alarm is sounded.

It should further be appreciated that a respiration monitor in accordance with the present invention can operate with other than radio frequency signals. For example, the monitor can operate on sonic or optical probe and reply signals where appropriate transducers are utilized to illuminate the subject and receive reflections therefrom.

What is claimed is:

1. Apparatus for monitoring the respiration of a subject comprising:
   first means for generating a probe signal and transmitting said probe signal to illuminate a body portion of said subject, a portion of said probe signal being reflected from said body portion;
   second means for receiving said reflected signal and generating an output signal indicative thereof;
   third means, responsive to a signal indicative of said probe signal and said second means output signal, for generating first and second output signals respectively indicative of the cosine and sine of the phase difference between said probe signal and said reflected signal; and
   fourth means, responsive to said third means first and second output signals, for deriving the time derivatives of said third means first and second output signals and generating an output signal only when said derivatives are concurrently substantially zero, whereby said fourth means output signal is indicative of instants of respiration extrema.

2. The apparatus of claim 1 further including fifth means, responsive to said third means first and second output signals and said fourth means output signal, for detecting the direction of motion of said body portion and generating an output signal indicative of a predetermined specie of respiration extrema.

3. The apparatus of claim 1, wherein said third means comprises first and second mixers and a phase shifter;
   said first mixer being responsive to said respective signals indicative of said probe signal and said reflected signal, and generating said third means first output signal;
   said phase shifter shifting the phase of a portion of said signal indicative of said probe signal by substantially 90°; and
   said second mixer being responsive to said phase shifted signal portion and said signal indicative of said reflected signal, and generating said third means second output signal.

4. The apparatus of claim 1 wherein said third means comprises:
   fifth means, for alternately shifting the phase of said signal indicative of said probe signal by a first phase and a second phase, at a periodic rate, the difference between said first and second phase being substantially 90°;
   sixth means, responsive to said phase shifted signal and said signal indicative of said reflected signal, for generating an output signal indicative of the cosine of the instantaneous phase difference therebetween;
   seventh means, responsive to said sixth means output signal, for generating first and second output signals, alternatively indicative of said sixth means instantaneous output signal in accordance with said periodic rate; and
   eighth means, responsive to said seventh means first and second output signals, for generating first and second output signals, respectively indicative of the envelopes of said seventh means first and second output signals;
   said eighth means first and second output signals being said third means output signals.

5. The apparatus of claim 4 further including ninth means for generating a signal indicative of said periodic rate and wherein;
   said fifth means comprises a voltage-controlled phase shifter responsive to said rate signal;
   said seventh means comprises a mixer;
   said seventh means comprises a multiplex switch, responsive to said rate signal and having two output terminals; and
   said eighth means comprises a pair of low pass filters, respectively coupled to said multiplex switch output terminals.

* * * * *